US008062643B2

(12) United States Patent
Schmidt

(10) Patent No.: US 8,062,643 B2
(45) Date of Patent: *Nov. 22, 2011

(54) USE OF NEUROTOXIN THERAPY FOR TREATMENT OF UROLOGIC AND RELATED DISORDERS

(75) Inventor: Richard A Schmidt, Arvada, CO (US)

(73) Assignee: The Regents of the University of Colorado, Boulder, CO (US)

( * ) Notice: Subject to any disclaimer, the term of this patent is extended or adjusted under 35 U.S.C. 154(b) by 711 days.

This patent is subject to a terminal disclaimer.

(21) Appl. No.: 11/925,938

(22) Filed: Oct. 27, 2007

(65) Prior Publication Data

US 2008/0177248 A1 Jul. 24, 2008

Related U.S. Application Data

(63) Continuation of application No. 10/981,015, filed on Nov. 3, 2004, which is a continuation of application No. 10/685,995, filed on Oct. 14, 2003, now Pat. No. 7,001,602, which is a continuation of application No. 09/978,982, filed on Oct. 15, 2001, now Pat. No. 6,667,041, which is a continuation of application No. 09/463,040, filed as application No. PCT/US98/14625 on Jul. 15, 1998, now Pat. No. 6,365,164.

(60) Provisional application No. 60/052,580, filed on Jul. 15, 1997.

(51) Int. Cl.
*A61K 39/08* (2006.01)
*A61K 39/02* (2006.01)
*A61K 49/00* (2006.01)

(52) U.S. Cl. .................. 424/239.1; 424/236.1; 424/9.1; 530/350; 514/2

(58) Field of Classification Search ............... 424/239.1, 424/9.1, 236.1; 514/2; 530/350
See application file for complete search history.

(56) References Cited

U.S. PATENT DOCUMENTS

| | | | |
|---|---|---|---|
| 4,932,936 A | 6/1990 | Dykstra et al. |
| 5,183,462 A | 2/1993 | Borodic |
| 5,437,291 A | 8/1995 | Pasricha et al. |
| 5,674,205 A | 10/1997 | Pasricha et al. |
| 5,837,265 A | 11/1998 | Montal et al. |
| 5,919,665 A | 7/1999 | Williams |
| 5,939,070 A | 8/1999 | Johnson et al. |
| 5,989,545 A | 11/1999 | Foster et al. |
| 6,306,423 B1 | 10/2001 | Donovan et al. |
| 6,312,708 B1 | 11/2001 | Donovan |
| 6,365,164 B1 | 4/2002 | Schmidt |
| 6,383,509 B1 | 5/2002 | Donovan et al. |
| 6,506,399 B2 | 1/2003 | Donovan |
| 6,585,993 B2 | 7/2003 | Donovan et al. |
| 6,667,041 B2 | 12/2003 | Schmidt |
| 6,939,852 B2 | 9/2005 | Graham |
| 7,001,602 B2 | 2/2006 | Schmidt |
| 7,153,514 B2 | 12/2006 | Schmidt | |
| 7,429,387 B2 * | 9/2008 | Schmidt | 424/239.1 |
| 7,449,192 B2 * | 11/2008 | Schmidt | 424/247.1 |
| 7,455,845 B2 * | 11/2008 | Schmidt | 424/247.1 |
| 7,470,431 B2 * | 12/2008 | Schmidt | 424/239.1 |
| 2004/0180065 A1 | 9/2004 | Schmidt | |
| 2005/0048084 A1 | 3/2005 | Schmidt | |
| 2005/0049175 A1 | 3/2005 | Schmidt | |
| 2005/0112147 A1 | 5/2005 | Schmidt | |
| 2005/0159337 A1 | 7/2005 | Schmidt | |
| 2005/0175636 A1 | 8/2005 | Donovan | |
| 2009/0004312 A1 | 1/2009 | Schmidt | |
| 2009/0028974 A1 | 1/2009 | Schmidt | |
| 2009/0068227 A1 | 3/2009 | Schmidt | |

FOREIGN PATENT DOCUMENTS

| | | |
|---|---|---|
| AU | 2005 234633 | 4/2007 |
| JP | 6-183975 | 7/1994 |
| JP | 8-511537 | 12/1996 |
| WO | WO 95/05842 | 3/1995 |
| WO | WO 95/17904 | 7/1995 |
| WO | WO 99/03483 | 1/1999 |

OTHER PUBLICATIONS

U.S. Appl. No. 11/925,942, filed Oct. 27, 2007 Schmidt.
U.S. Appl. No. 11/925,945, filed Oct. 27, 2007 Schmidt.
"AFUD Prostate Cancer Treatment: Treatment"; American Foundation for Urologic Disease; (at least as early as Aug. 5, 2003).
"Continence Management"; The Prostate Cancer Charity; (at least as early as Aug. 8, 2003); 6 pp.
"Inconsistence and the Prostate"; Phoenix5; (at least as early as Aug. 5, 2003); 11 pp.
"Prostate Cancer (PDQ®): Treatment"; National Cancer Institute; (Jul. 17, 2003); 11 pp.
"Prostate Cancer: Prostate Cancer Transrectal Biopsies"; (at least as early as Aug. 20, 2003); 9 pp.
"Prostate Cancer: Tumor Grading"; UPMC Cancer Centers; (2003); 2 pp.
"Prostate Cancer: What are the Treatment Options?"; NSW Health; (Jan. 4, 2002); 2 pp.
"Prostate Gland and Urinary Problems"; Better Health Channel; (Oct. 10, 2001); 10 pp.
"Questions and Answers About the Prostate-Specific Antigen (PSA) Test"; National Cancer Institute; (Jan. 11, 2001); 5 pp.
"Symptoms & Treatments"; Multiple Sclerosis International Federation; pp. 1-6; (as early as 2003). "The Side Effects of Treatment"; Varian Medical System; (1999-2003); 2 pp.
"Treating Prostate Disease"; The Cleveland Clinic; (Jan. 28, 1999); 3 pp.
"Understanding Gleason Grading"; Phoenix5; (May 14, 1997); 8 pp.
"Western Multiple Sclerosis Center's Glossary; UW Medicine"; (at least before Sep. 30, 2003); 15 pp.
1996 MIMS Annual, Australian Edition. The entry for Botulinum Toxin is located at 5-372.
Amarenco, Lae Revue du Praticien (Paris) 1995 45:343-45.
Amarenco, "Evaluation et Traitment des Dysfoctionnements Vesico-Sphincteriens Neurogenes" Annales d'Urologie 27 (1993) pp. 313-320.
Araki et al. Detrusor-Sphincter Dyssynergia with Special Reference to its Diagnosis and Treatment, J. Saitama Med. School, 1992, 23-27, vol. 19, Department of Urology, Saitama Medical School, Moroyama, Iruma-gun, Saitama, Japan (partial translation).

(Continued)

*Primary Examiner* — Chih-Min Kam
(74) *Attorney, Agent, or Firm* — Hal Gibson; Debra Condino

(57) ABSTRACT

The present invention related to methods for treating neurological-urological conditions. This is accomplished by administration of at least one neurotoxin.

21 Claims, No Drawings

OTHER PUBLICATIONS

Bardsley; "The Neurogenic Bladder"; Art & Science Continence; (Jan. 7, 2000); pp. 39-41.
Beleggia et al., Arch. It. Urol., LXIX, (S.1): 61-63, 1997 (English Abstract).
Bladderinfo.com: Bladder Control Problems 2004 Pfizer, Inc. www.overactivebladderhelp.com/conditions/problems_bladder.htm, pp. 1-3.
BladderZone.com: Bladder Problems Explained, Pfizer, Ltd., www.bladderzone.com/info/bladder_expl.htm, Copyright 2003, pp. 1-2.
Borodic and Pearce, "New Concepts in Botulinum Toxin Therapy", Drug Safety 11 (1994), pp. 145 to 152.
Boyd, et al., Lancet 1996 348:481-82.
Bulau, Itherapeutische Perspektiven mit Botulinumtoxin Type A, Neurologie und Rehabilitation, Band 3, Heft 1 (1997) pp. 55-56. (including translation).
Burnstein et al.; "Prostatitis: A Difficult Diagnosis"; DeKalb Clinic Urology; (at least as early as Aug. 20, 2003); 3 pp.
Carl, Stefan, Affidavit, Sep. 26, 2006.
Chancellor et al., J Urol Apr. 2003;169 (Supp 4):351.
Crawford; "Prostate Cancer"; Best Doctors; (Jun. 7, 2000); 6 pp.
DasGupta et al., Urogynaecology 2003, 13:293-299.
Doggweiler et al.: The Prostate, vol. 37, No. 1, pp. 44-50 (1998).
Dykstra et al., Arch. Phys. Med. Rehabil., 71:24-26 (1990).
Dykstra et al.; "Effects of Botulinum a Toxin on Detrusor-Sphincter Dyssynergia in Spinal Cord Injury Patients"; J. Urology; 139:919-922; (May 1988).
Epstein;"Gleason Score 2-4 Adenocarcinoma of the Prostate on Needle Biopsy"; American Journal of Surgical Pathology; (2000) vol. 24(4); pp. 477-478.
Fowler C J et al: "Myotonic-Like EMG Activity of the Urethral Sphincter in Women With Urinary Retention and the use of Botulinum Toxin to Treat This Disorder" Neurophysiologie Clinique, vol. 20, No. Suppl, 1990, p. 19S, XP009058311 & 5th European Congress of Clinical Neurophysiology, Paris, France, Sep. 9-12, 1990. Neurophysiol.
Fowler et al., British J of Urol., Oct. 22, 1992, vol. 70, 387-389.
Grise, Phillippe, Affidavit, Sep. 26, 2006.
Grosse, Joachim, Affidavit, Sep. 25, 2006.
Han et al., "Botulinum toxin A injection for the treatment of detrusor external sphincter dyssynergia", (translated abstract), Apr. 2006, pp. 1-3.
Harrison, Principles of Internal Medicine 11th Edition 1987 in particular, pp. 196-197.
Internet presentation on prostate disorders and the anatomy of the prostate/bladder: http://www.farnilydoctor.co.uk/htdocs/PROSTATE/PROSTATE-specimen.html (printed on Dec. 11, 2006).
Internet presentation on prostatitis: http://www.urologyhealth.org/adult/index.cfm?cat=07&topic=I15 (printed on Dec. 11, 2006).
Ishizuka et al., J. Urology, 154:611-616 (1995).
Jankovic J. Related Articles, Links Botulinum toxin in movement disorders. Curr Opin Neurol. Aug. 1994;7(4):358-66.
Jankovic, J, Therapeutic Uses of Botulinum Toxin, NEJM 1991 324(17):1186-94.
Joo et al., Dis. Colon. Rectum, 39:1107-1111 (1996).
Karp Barbara Illowsky et al: "Therapeutic effects of botulinum toxins" 1995, Handbook of Natural Toxins; Bacterial Toxins and Virulence Factors in Disease Marcel Dekker, Inc., New York pp. 1-22.
Khastgir and Shah, Urology News 2001 5:6-8.
Kuo, Hann-Chorng, J Urol Nov. 2003, 170:1908-1912.
Leippold et al., Eur Urol 44 (2003) 165-174.
Maggi et al., J. Urol., 142:150-154 (1989).
Maria et al.; "Relief by Botulinum Toxin of Voiding Dysfunction Due to Prostatitis"; The Lancet; vol. 352, No. 9128, Aug. 1998 p. 625.
Marieb; "Chapter 13: Peripheral Nervous System and Reflex Activity"; Human Anatomy and Physiology, 5th Ed.; (at least as early as Aug. 8, 2003) 5 pp.
Martinez Pinero et al., Pelvic Plexus Denervation in Rats Causes Morphologic and Functional Changes of the Prostate, The Journal of Urology 150 (1993), pp. 215-218.
Medical Pharmacology at a Glance, Blackwell Scientific Publications,1987—pp. 18-19.

MS-Network.com Glossary, Section C; Benecke NI; 2000, pp. 1-4.
Nanninga, John B., Oxins (1993) p. 589-590.
Peak; "Understanding Continence"; The Interdisciplinary Journal of Rehabilitation; (Mar. 2002); 9 pp.
Punch, Gynaecological, and non-gynaecological, chronic pelvic pain, The Lancet, Feb. 21, 1998, 607, vol. 351, Department of OB/BYN, University of Michigan Medical Center, Women's Hospital, Ann Arbor, Michigan, USA.
Schurch et al.; "Effects of Botulinum A Toxin on the Periurethral Striated Spincter of the Neurogenic Bladder: Preliminary Study"; J. Urology; 96(7):375-80; (1990).
Shapiro et al, "Quantifying the smooth muscle content of the prostate . . . ", The Journal of Urology 147 (1992), pp. 1167 to 1170.
Smith et al., Int Urogynecol J (2002) 13:55-56.
Steinhardt, et al, Botulinum Toxin: Novel Treatment for Dramatic Urethral Dilatation Associated with Dysfuntional Voiding, J. Urol. 1997 158:190-91.
Striker; "Special Communication: Kuh Notes"; J. Urology; 136:919; (Oct. 1986).
Strum; "Is There a Correct Way to Treat Prostate Cancer"; Prostate Cancer Research Institute; 28 pp. (at least as early as Sep. 12, 2000).
Strum; "Preductive and Prognostic Information in the Counseling of Patients Recently Diagnosed with Prostate Cancer"; The Prostate Cancer Research Institute; (at least as early as Sep. 12, 2000); 21 pp.
Treatment for Localized Disease: Observation and Monitoring of PSA; Prostate Cancer Research Institute; (at least as early as Aug. 11, 2003); 1 p.
Zwergel Ulrike et al: "Bladder dysfunction in disseminated encephalomyelitis—Drug therapy and interventional methods" Fortschritte Der Neurologie Psychiatrie, vol. 63, No. 12, 1995, pp. 495-503 (including translation).
Albers et al. "Limb Myokymia" Muscle and Nerve. Nov./Dec. 1981,4 (6):494-504.
Sweeney et al. "Intravesical Instillation of Botulinum Toxin A for Overactive Bladder", International Continence Society 35th Annual Meeting, Aug. 28-Sep. 2, 2005, Montreal, Canada, Meeting Abstract, p. 565.
Abrams, "The Standardisation of Terminology of Lower Urinary Tract Function", Scand. J Urol. Nephrol, 1988; Supp 114:5-19.
"Incontinence—1st International Consultation on Incontinence" edited by Abrams P,Khoury Sand Wein A, Health Publication Ltd, 1999, 8 pages.
Abrams, The Standardisation of Terminology of Lower Urinary Tract Function: Report from the Standardisation Sub-committee of the International Continence Society, Neurourology and Urodynamics 2002; 21:167-178.
Scott et al. "Botulinum A toxin injection as a treatment for blepharospasm", Arch Ophthalmol,1985; 103:347-350.
Ewing et al., "Subtrigonal Phenol Injection for Urge Incontinence Secondary to Detrusor Instability in Females", British Journal of Urology, 1982, vol. 54, pp. 689-692.
Declaration by Professor Peter Lawrence Dwyer, Jul. 7, 2009.
CV of Professor Peter Lawrence Dwyer, Jul. 7, 2009.
Urinary Tract Diagram, viewed May 12, 2008.
Pasricha, et al. Botulinum toxin for achalasia: long-term outcome and predictors of response Gastroenterology. May 1996;110(5):1410-5.
Carpenter, Motor Responses of the Urinary Bladder and Skeletal Muscle in *Botulinum* Intoxicated Rats, J. Physiol. 1967 188:1-11.
Urinary incontinence in children, National Kidney and Urologic Diseases Information Clearing House, available at http://kidney.niddk.nih.gov/kudiseases/pubs/uichildren/, Oct. 2006.
Second Declaration by Professor Peter Lawrence Dwyer, Feb. 23, 2010.
R. Duane Cespedes, C. A. Cross and E. J. McGuire, Modified Ingelman-Sundberg Bladder Denervation Procedure for intractable Urge Incontinence, *The Journal of Urology*, vol. 156,1744-1747, Nov. 1996.
R. Spernol, P. Riss, Urodynamische Überprüfung der Neuraltherapie bei motorischer und sensorischer Reizblase *Geburtsh. u. Frauenheilk.* 42 (1982), 527-529.
M. J. Torrens and H. B. Griffith, The Control of the Uninhibited Bladder by Selective Sacral Neurectomy *British Journal of Urology* (1974), 46, 639-644.

JM Gracies, E. Elovic, J. McGuire, D. Simpson, Traditional Pharmacological Treatments for Spasticity Part I: Local Treatments *Muscle & Nerve*, Supplement 6, 1997, S61 to S91.

J. Borg-Stein, J. Stein, Pharmacology of botulinum toxin and implications for use in disorders of muscle Tone, *Journal of Head Trauma Rehabilitation* Sep. 1993, 103-106.

La Koman, JF Mooney, B. Paterson Smith, Neuromuscular Blockade in the Management of Cerebral Palsy, *Journal of Child Neurology* vol. 11 1996, S23-S28.

Bruschini et al., "Neurologic control of prostatic secretion in the dog." Invest. Urol., 15(4):288-290 (1978).

Downie et al., "Evidence for a spinal site of action of clonidine on somatic and viscerosomatic reflex activity evoked on the pudendal nerve in cats." J. Pharmacol. Exp. Ther., 246(1):352-358 (1988).

Entry for "benigne Prostatahyperblasie" in Pschyrembel, klinisches Wörterbuch (257. Auflage, 1994). 2 pages.

Håkanson et al., "Multiple tachykinin pools in sensory nerve fibres in the rabbit iris" Neuroscience, 21(3):943-950 (1987).

Higgins et al., "Studies on the structure and intrinsic innervation of the normal human prostate." Prostate Suppl., 2:5-16 (1989).

Lepor "Role of long-acting selective alpha-1 blockers in the treatment of benign prostatic hyperplasia" Urol. Clin. North Am., 17(3):651-658 (1990).

Mocchetti, "Pharmacology of neuronal gene expression." Pharmacol. Res., 21(2):85-95 (1989).

Schurch et al., "Botulinum-A toxin as a treatment of detrusor-sphincter dyssynergia: a prospective study in 24 spinal cord injury patients." J. Urol., 155:1023-1029 (1996).

Tim et al.,"Botulinum toxin therapy for neurologic disorders." Postgrad Med. May 1, 1992;91(6):327-32, 334.

Statutory Declaration of Jeffrey Thavaseelan relating to Australian Patent Application No. 2005234633, Aug. 2, 2010.

Curriculum vitae—Mr. Jeffrey Thavaseelan, Aug. 2, 2010 (Exhibit JT-1).

British Journal of Urology International, Feb. 2005 Supplement 1, V. 95, Abstract UO16 (Exhibit JT-2).

Abrams, The Standardisation of Terminology of Lower Urinary Tract Function: Report from the Standardisation Sub-committee of the International Continence Society, Neurourology and Urodynamics 2002; 21:167-178 (Exhibit JT-3).

Marieb; Human Anatomy & Physiology 5th edition, Benjamin Cummings, San Francisco 2001; available at website for Owensboro Community & Technical College as part of course notes for urinary anatomy http://legacy.owensboro.kctcs.edu/gcaplan/anat2/notes/Notes3%20urinary%20anatomy.htm (Exhibit JT-4).

Bladder Management for Adults with Spinal Cord Injury a Clinical Practice Guideline for Health-Care Providers; 2006, Consortium for Spinal Cord Medicine, Clinical Practice Guidelines, 2006, pp. 3-35 (Exhibit JT-5).

Hirayama, et al., Positive response to ice water test associated with high-grade bladder outlet obstruction in patients with benign prostatic hyperplasia, Urology. 2003 62(5):909-13. (Exhibit JT-6).

Ishigooka, et al.,Electrical pelvic floor stimulation: a possible alternative treatment for reflex urinary incontinence in patients with spinal cord injury, Spinal Cord 1996 34(7):411-15.

Nygaard, et al., Spine update. Urological management in patients with spinal cord injuries. Spine (Phila Pa 1976). 1996 ;21(1):128-32.

Zermann, et al., Möglichkeiten der Therapie and Rehabilitation von Patienten mit Harninkontinenz [Possibilities of therapy and rehabilitation of patients with urinary incontinence] Z Arztl Fortbild (Jena). 1996 90(6):533-7, including abstract in English.

Voiding Dysfunction, Diagnosis and Treatment, Rodney A. Appell, ed., 2000 Humana Press, Inc., content vii.

Mertens, et al., Long-term clinical, electrophysiological and urodynamic effects of chronic intrathecal baclofen infusion for treatment of spinal spasticity, Acta Neurochir Suppl. 1995;64:17-25.

"Treatment How is Prostate Cancer Treated?", American Foundation for Urologic Disease, available at http://www.afud.org/conditions/pctreat.html, printed Aug. 5, 2003, pp. 1-2.

"Continence Management"; The Prostate Cancer Charity; available at http://www,prostate-cancer.org.uk/learn/prostateCancer/livingWith/continenceManagement.asp, printed Aug. 8, 2003, pp. 1-6.

"Incontinence & the Prostate", from Morgenstern Urology Clinic & Men's Health Center, Phoenix5, available at http://www.phoenix5.org/Basics/treatsides/incontinence/incontMorganstern.html, printed Aug. 5, 2003, pp. 1-11.

"Prostate Cancer (PDQ®): Treatment"; National Cancer Institute, available at http://www.cancer.gov/cancerinfo/pdq/treatment/prostate, date last modified Jul. 17, 2003, pp. 1-11.

"Prostate Cancer: prostate cancer transrectel biopsies"; available at http://216.239.41.104/search?q=cache:RUEZIFhOxiAJ:www.listure.com/prostate-cancer/pro..., printed Aug. 20, 2003, pp. 1-9.

"Prostate Cancer: Tumor Grading"; University of Pittsburgh Medical Center Cancer Centers, available at http://www.upmccancercenters.com/cancer/prostate/gradingsystems.html. printed Aug. 11, 2003, pp. 1-2.

"Prostate Cancer: What are the Treatment Options?"; NSW Health, publication No. BHC-6055, available at http://www.mhcs.health.nsw.gov.au/health-public-affairs/mhcs/publications/6055.html, publication date Jan. 4, 2002, pp. 1-2.

"Prostate Gland and Urinary Problems"; Better Health Channel, available at http://www.betterhealth.vic.gov.au/bhcv2/bhcarticles.nsf/pages/Prostate_gland_and_urinary_p..., article publication date Oct. 10, 2001, pp. 1-4.

"Questions and Answers About the Prostate-Specific Antigen (PSA) Test"; National Cancer Institute, available at http://cis.nci.nih.gov/fact/5_29.htm, date reviewed Jan. 11, 2001, pp. 1-5.

"Symptoms & Treatments Bladder Management in Multiple Sclerosis"; Multiple Sclerosis International Federation, available at http://www.msif.org/en/symptoms_treatments/ms_by_topic/continence/articles/bladder_man... printed Sep. 30, 2003, pp. 1-6.

"The Side Effects of Treatment"; Varian Medical System, available at http://www.varian.com/pti/cty102c.html, printed Aug. 5, 2003, pp. 1-2.

"Treating Prostate Disease"; The Cleveland Clinic, available at http://www.clevelandclinic.org/quality/08-12/08-12c.htm, dated Jan. 28, 1999, pp. 1-3.

"Understanding Gleason Grading"; Phoenix5, available at http://www.phoenix5.org/Infolink/GleasonGrading.html, last revised May 14; 1997, pages 1-6.

"Western Multiple Sclerosis Center's Glossary"; UW Medicine, available at http://216.239.53.104/Search?q=cache:tbApZaM3_5kJ:www.washington.edu/medicine/patien..., printed Sep. 30, 2003, pp. 1-15.

* cited by examiner

USE OF NEUROTOXIN THERAPY FOR TREATMENT OF UROLOGIC AND RELATED DISORDERS

This application is a continuation of U.S. patent application Ser. No. 10/981,015, filed Nov. 3, 2004, which is a continuation of U.S. patent application Ser. No. 10/685,995, filed Oct. 14, 2003, now U.S. Pat. No. 7,001,602, which is a continuation of U.S. patent application Ser. No. 09/978,982, filed Oct. 15, 2001, now U.S. Pat. No. 6,667,041, which is a continuation of U.S. patent application Ser. No. 09/463,040, filed Jan. 17, 2000, now U.S. Pat. No. 6,365,164, which is a 371 of PCT Application No. PCT/US98/14625, filed Jul. 15, 1998, which claims priority under 35 U.S.C. §119(e) to U.S. Provisional Application Ser. No. 60/052,580, filed Jul. 15, 1997. The entire disclosure of each of the above-identified applications is incorporated herein by reference.

FIELD OF THE INVENTION

The present invention provides methods for treating neuronally-mediated urologic and related disorders, for example, benign prostatic hyperplasia (BPH) and prostatitis. This is accomplished by administering a composition that includes at least one neurotoxic compound or by conventional therapies.

BACKGROUND OF THE INVENTION

Many medical conditions in urology are rooted in a spastic dysfunction of the sacral reflex arcs. Examples of such conditions include pelvic pain (e.g., interstitial cystitis, endometriosis, prostatodynia, urethral instability syndromes), pelvic myofascial elements (e.g., levator sphincter, dysmenorrhea, anal fistula, hemorrhoid), urinary incontinence (e.g., unstable bladder, unstable sphincter), prostate disorders (e.g., BPH, prostatitis, prostate cancer), recurrent infection (secondary to sphincter spasticity), and urinary retention (secondary to spastic sphincter, hypertrophied bladder neck) and neurogenic bladder dysfunction (e.g., Parkinson's Disease, spinal cord injury, stroke, multiple sclerosis, spasm reflex).

The prostate is a partially glandular and partially fibromuscular gland of the male reproductive system. During aging, the prostate tends to enlarge (hypertrophy). This prostatic enlargement can lead to urethral obstruction and voiding dysfunction.

Prostatic enlargement is a common occurrence in older men. Lytton et al. (Lytton, B., Emery, J. M. and Harvard, B. M. [1973] 99: 639-645) estimated that a 45 year old male had a 10% risk of prostate surgery by age 70. The U.S. Census Report estimates that there are 30 million people today over age 65. This segment of the population is projected to rise to 50 million over the next 30 years. Therefore, the number of men with prostatic enlargement also will increase. According to draft reports of the National Kidney and Urologic Disease Advisory Board, 425,000 prostatectomies were performed in the United States in 1989. Based on population growth estimates, the number of prostatectomies performed annually will rise to 800,000/year by the year 2020.

The urethra passes through the prostate (prostatic urethra) as it courses to the external urethral orifice. The prostate has five distinct lobes that are apparent at 12 weeks in the human fetus (Lowsley, O. S. Am. J. Anat. [1912] 13: 299-349.). Although the lobular branching found in the fetus is not visible in the prepubescent prostate, the lateral middle anterior and posterior lobes are used to describe the enlarged prostate.

A more recent viewpoint is that the prostate also is comprised of several morphologically distinct zones (McNeal, J. Urol. Clin. North Am. [1990] 17(3): 477-486). The majority of the glandular volume is composed of the peripheral zone (~70-75%). The remainder of glandular volume is divided into the central zone (~20-25%), the transition zone (~5-10%) and the periurethral glandular zone (~1%).

McNeal (1990) reported that BPH develops in the transition zone and the periurethral glandular zone. BPH nodules develop either within or immediately adjacent to the preprostatic sphincteric zone. The transition zone is a small region close to the urethra intimately related to the proximal urethral sphincter. The stroma of the transition zone is dense and compact, and is unusually susceptible to neurologically-induced disturbances of growth control. Its glands penetrate the sphincter, while sphincter muscle fibers penetrate the transition stroma. The periurethral glandular zone has a similar urogenic sinus origin as the transition zone.

BPH may be associated with increased amounts of stroma relative to epithelium (Bartsch, G., Muller, H. R., Oberholzer, M., Rohr, H. P., J. Urol. [1979] 122: 487-491). A significant portion of the stroma is smooth muscle (McNeal, 1990) which is under sympathetic nervous control. The contractile properties of this smooth muscle could account for the dynamic component of obstruction in BPH (Bruschini, H. et al. [1978] Invest. Urol. 15(4): 288-90; Lepor, H. [1990] Urol. Clin. North Am. 17(3): 651-658).

In addition to sympathetic control of prostatic stroma, the prostate is highly innervated. The prostate nerve fibers enter the prostate from the posterior lateral aspect, with a concentration of ganglia near the junction between the prostate and the seminal vesicles (Maggi, C. A., ed. [1993] Nervous control of the Urogenital System, Harwood Academic Publishers; Higgins, J. R. A. and Gosling, J. A. [1989] Prostate Suppl. 2: 5-16).

Acetylcholine (ACH), neuropeptide Y (NPY), vasoactive intestinal peptide (VIP) and noradrenaline fibers have been described in this gland. A rich plexus of ACH-positive nerve cell bodies is associated with secretory acini in all parts of the gland. Some of the ACH fibers also contain NPY neurons. VIP-containing neurons have been found associated with ACH-containing nerve cell bodies. Occasional neurons have been found between the ACH-staining nerve fibers, suggesting that both NPY and noradrenergic neurons supply smooth muscle (Higgins, J. R. A. and Gosling, J. A. [1989] Prostate Suppl. 2: 5-16).

Autonomic nerves are distributed evenly between the central and peripheral zones of the prostate (Higgins, J. R. A. and Gosling, J. A. [1989] Prostate Suppl. 2: 5-16). Peripheral neuronal control is similar. In addition, there is no difference in the type of nerve fibers found associated with either epithelial or stromal elements of the gland.

The anatomical studies of nerve fiber types in the prostate, coupled with other studies of innervation of prostatic stroma (Brushing H., Schmidt, R. A., Tanagho, E. A., [1978] Invest. Urol. 15(4): 288-290; Watanabe, H., Shima, M., Kojima, M., Ohe, H. L. [1989] Pharmacol. Res. 21(Suppl 2): 85-94) suggest that cholinergic innervation influences epithelial behavior, while adrenergic innervation influences stromal tonus (excitability). These observations have provided a rationale for the use of, for example, alpha blockers in the treatment of BPH. The effects of alpha blockers (Downie, J. W. and Bialik, G. J. [1988] J. Pharmacol. Exp. Ther. 246(1): 352-358) can also account for improvements in symptoms of BPH as a result of dampening of dysfunctional striated sphincter behavior by the alpha blockers.

Studies have also shown that there are several tachykinins (for example, substance P [SP], calcitonin gene related peptide [CGRP], neurokinin A, bradykinin, and nerve growth factor [NGF]) that can influence the tonus of smooth muscle (Hakanson, et al., [1987] Neuroscience 21(3): 943-950). Neurotransmitter receptors have been quantified throughout the prostate (e.g., NPY, VIP, SP, leu-enkephalin (L-enk), met-enkephalin, 5-HT, somatostatin, acetylcholinesterase positive fibers (ACTH), and dopamine beta-hydroxylase (DBH) (Crowe, R., Chapple, C. R., Burnstock, G. The Human Prostate Gland: A Histochemical and Immunohistochemical Study of Neuropeptides, Serotonins, Dopamine beta-Hydroxylase and Acetylcholinesterase in Autonomic Nerves and Ganglia). There is some variation in receptor density at different prostatic sites in benign prostatic hyperplasia.

Changes in electrophysiologically recorded cellular behavior and in concentration of neuropeptides within the spinal cord have been shown to be a secondary consequence of mechanical pinch to the tail muscles of a rat, catheter stimulation of the posterior urethra, and electrostimulation of a peripheral nerve. Dyssynergia between the detrusor and the urethral sphincter is a significant finding in prostatodynia patients. Denervation of the prostate has been shown to produce dramatic changes within the prostatic epithelium. Thus there is evidence that experimentally induced alterations in neurological influences can be produced in the sacral, spinal cord, bladder or urethra through mechano-, electro-, chemical or thermal (microwave, laser) methods to change irritative behavior. However, there have been no known attempts to use neurotoxins for therapeutic applications.

There is poor correlation between the degree of prostatic enlargement and the severity of symptoms. While 80% of men age 70 show BPH on transrectal ultrasound scans, only 20% seek surgery (Coffey, D. S. and Walsh, P. C. [1990] Urol. Clin. North Am. 17(3): 461-475), the treatment of choice for BPH (Fowler, F. J. Jr., Wennberg, J. E., Timothy, R. P. [1988] J. Amer. Med. Assoc., 259(20): 3022-3028). Symptoms of irritation may far exceed symptoms expected based on the size of the prostate. Symptoms may improve after surgical treatment of BPH by procedures such as transurethral resection of the prostate (TURP) (Christensen, Aagaard, M. M. J., Madsen, P. O. [1990] Urol. Clin. North Am. 17(3): 621-629), balloon dilation (Dowd, J. B. and Smith, J. J. III [1990] Urol. Clin. North Am. 17(3): 671-677), or prostatic hyperthermia (Baert, L., Ameye, F., Willemen, P., et al., [1990] J. Urol. 144: 1383-1386). However, symptoms persist in as many as 15% of all BPH patients (Baert, L., Ameye, F., Willemen, P., et al., [1990] J. Urol. 144: 1383-1386; Wennberg, J. E., Mullly, A. G., Hanley, D., Timothy, R. P., Fowler, F. J., Roos, R. P., Barry, M. J. et al., [1988] J. Amer. Med. Assoc. 259: 3027-3030). Up to 25% of BPH patients have secondary procedures in long term follow-up studies, suggesting that surgical approaches do not address the fundamental mechanisms that produce BPH, i.e., the faulty neurological influence (control mechanism) on the integrity of the lower urinary tract.

The need for repeated surgeries, the morbidity and mortality associated with TURP and the cost of surgery have led to the development of some non-surgical approaches such as androgen ablation (McConnell, J. D., [1990] Urol. Clin. North Am. 17(3): 661-670) and the use of alpha blockers discussed above, but few medical or surgical treatments to date have produced a restoration of void behavior to normal state (flow rate of about 25 cc/sec and void volume of about 400 cc).

The present invention uses chemical and non-chemical methods, particularly neurotoxins, to modulate neuronally-mediated urologic and related disorders. For example, such methods can be used to treat BPH and related conditions such as prostatitis. The instant invention also may remove triggers of changes in the CNS by non-chemical methods including biofeedback, or by chemical methods that treat BPH and other urological conditions by the administration of substances that block various neurological activities, such as, for example, selected neurotoxins.

OBJECTS AND SUMMARY OF THE PRESENT INVENTION

It is an object of the instant invention to provide safe, inexpensive, out patient methods for the prevention and treatment of urological-neurological dysfunctional states or conditions, for example, prostatic enlargement.

It is a further object of the present invention to provide compositions for this therapeutic goal. It is a still further object of the present invention to provide dosages and methods of administration for compositions useful for the prevention and treatment of neurological-urological conditions.

Other objects of the present invention will be readily apparent to those of ordinary skill in the art.

In accordance with one aspect of the present invention, there are provided methods of treating urological-neurological conditions in mammals, said methods comprising the step of administering a therapeutically effective amount of at least one neurotoxin to such a mammal. It is preferred that the neurotoxin inhibits synaptic function. Such inhibition produces selective denervation, and, for example, atrophy of the prostate and reversal of irritative symptoms associated with prostatic enlargement. In one embodiment of the instant invention, the neurotoxin induces dysfunction of the presynaptic neuronal terminal by specific binding and blockade of acetylcholine release at myoneural junctions. Such a neurotoxin can be, for example, botulinum toxin type A (e.g., BOTOX®, Allergan).

Preferably, the neurotoxin is safe, highly selective and easy to deliver, including when combined with other therapies. Other useful neurotoxins include capsaicin, resinoferatoxin and α-bungotoxin. Delivery of the neurotoxin can be by any suitable means. A convenient and localized method of delivery is by injection.

A therapeutically effective amount of the neurotoxin is the dosage sufficient to inhibit neuronal activity for at least one week, more preferably one month, most preferably for approximately 6 to 8 months or longer. Dosing can be single dosage or cumulative (serial dosing), and can be readily determined by one skilled in the art. Neurotoxin can be delivered serially (i.e., one time per month, one time per every six months) so that the therapeutic effect can be optimized. Such a dosage schedule is readily determined by one skilled in the art based on, e.g., patient size and the condition to be treated, and will depend on many factors, including the neurotoxin selected, the condition to be treated, the degree of irritation, and other variables. One suggested course of treatment for BPH is 200 units every three days up to the LD50 for Botox or about 2500 units.

The aforementioned methods of treatment should be particularly useful for the long-term control of neurological-urological disorders, e.g., the symptoms of prostatic enlargement, without the need for surgical intervention. Furthermore, the methods of the instant invention provide for control of neurological-urological disorders, e.g., BPH and related conditions, in a highly selective manner, without the potential side effects and treatment failures associated with current treatment modalities.

DETAILED DESCRIPTION OF THE PREFERRED EMBODIMENT

"Urological-neurological condition or disorder" includes many medical conditions in urology rooted in a spastic dysfunction and/or degeneration of the sacral reflex arcs. Examples of such conditions include pelvic pain (e.g., interstitial cystitis, endometriosis, prostatodynia, urethral instability syndromes), pelvic myofascial elements (e.g., levator sphincter, dysmenorrhea, anal fistula, hemorrhoid), urinary incontinence (e.g., motor or sensory, unstable bladder, unstable sphincter), prostate disorders (e.g., BPH, prostate cancer), recurrent infection (secondary to sphincter spasticity), and urinary retention (secondary to spastic sphincter, hypertrophied bladder neck), and neurogenic bladder dysfunction (e.g., Parkinson's Disease, spinal cord injury, stroke, multiple sclerosis, spasm reflex) and other such urological conditions of a nervous etiology.

The prostatic enlargement that can be treated according to the methods of the instant invention can be of any etiology. The instant invention is particularly suited for the treatment of prostatic hyperplasia, especially benign prostatic hyperplasia. The present invention can also be used for the treatment of enlargement of the prostate with inflammation (prostatitis), particularly abacterial prostatitis. In addition, the methods of the instant invention can be used for the treatment of prostatodynia.

Without being bound by theory, the basis for the treatment of the neurological-urological conditions according to the instant invention is the removal or modulation of the neural basis for the dysfunctional regulation of the affected tissue. For example, the modulation of the neural basis of prostate glandular dysfunction can be accomplished by any non-surgical means known in the art. Such means can include, for example, biofeedback, α-blockers, pharmacological methods, and the use of one or more neurotoxins to inhibit synaptic function in the affected gland. It is preferred that the neurotoxin cause long-lasting inhibition of synaptic function, preferably greater than one week, more preferably greater than one month, most preferably six to eight months or longer. Such neurotoxins can include, for example, capsaicin, resinoferatoxin, α-bungotoxin, terodotoxin and botulinum toxin. Botulinum toxin is a preferred neurotoxin according to the instant invention, particularly botulinum toxin A, more particularly BOTOX® (Allergan).

The toxin can be formulated in any pharmaceutically acceptable formulation in any pharmaceutically acceptable form. Such forms and formulations include liquids, powders, creams, emulsions, pills, troches, suppositories, suspensions, solutions, and the like. The toxin can also be used in any pharmaceutically acceptable form supplied by any manufacturer.

In a preferred embodiment in accordance with the method of the instant invention, the neurotoxin is botulinum toxin type A. Therapeutically effective amounts of botulinum toxin can be any amounts or doses that are less than a toxic dose, for example, less than about 3000 IU/70 kg male, preferably between 100 IU/70 kg male to 1200 IU/70 kg. The dosages can be given as a single dose, or as divided doses, for example, divided over the course of four weeks.

The neurotoxins of the instant invention can be administered by any suitable means. In the preferred embodiment of the invention, botulinum toxin is administered by injection. Such injection can be administered to any affected area. For example, the neurotoxin can be injected urethroscopically into the prostate with 200 IU with single or serial dosing. Preferably, the neurotoxin is injected every three days until a therapeutic effect is achieved or up to about 2500 units.

The following techniques are used in this invention:

Tissue Preparation for Light Microscopy

Tissues are fixed in 6% paraformaldehyde in 0.1 M phosphate buffer, pH 7.2, for 24 hours, dehydrated in graded alcohol and xylene, and embedded in paraffin. Sections are cut and stained with appropriate stains, such as hematoxylin/eosin.

Tissue Preparation for Electron Microscopy

Tissues are collected and fixed in 2.5% glutaraldehyde in 0.1 M phosphate buffer, pH 7.2, for 1 hour at 4° C., then incubated with 0.1% osmium tetroxide for 1 hour and embedded in EPON. Ultrathin sections (80 nm) are prepared and stained with lead citrate/uranyl acetate and examined with an electron microscope (Philips, model 201).

Tunel Stain for Apoptosis

The tissue is fixed and embedded as described above. The tissues are deparaffinized and reacted with Proteinase K (Boehringer). They are further treated with peroxidase and TDT enzyme and placed in a humidifier set at 37° C. for one hour. The sections are washed and anti-digoxigenin-peroxidase is added for 30 minutes, followed by staining with nickel-DAB (diaminobenzene).

Immunohistochemistry Studies

The presence of the neuropeptides VIP, SP, NPY, L-Enk and calcitonin gene-related peptide (CGRP) as well as the expression of transforming growth factor beta (TGF-beta), transforming growth factor alpha (TGF-alpha), epidermal growth factor (EGF) and basic fibroblast growth factor (bFGF) are determined in prostatic tissues using appropriate monoclonal antibodies. Use of neurotoxins results in prostatic atrophy, which should be reflected by lower levels of growth factors in treated prostatic tissue.

Sections are incubated overnight at room temperature with primary antibodies followed by immunostaining with avidin-biotin-peroxidase (Vectastain Elite ABC, Vector Labs, USA). Rabbit polyclonal antiserum against the neurotransmitters VIP, CGRP, SP, NPY and L-Enk (Peninsula Labs, USA) is used in these preparations, at dilutions of 1:8000 to 1:12,000. Immunocytochemical controls consist of preabsorbing the primary antiserum with appropriate antigen, or their substitution with normal serum (Blasi, J., Chapman, E. R., Yamaskai, S., Binz, T., Niemann, H and Jahn, R. [1993] The EMBO Journal 12: 4821-4828; Black, J. D. and Dolly, J. O. [1986] J. Cell Biol. 103; 535-544; Linial, M. [1995] Is. J. Med. Sci. 31: 591-595). After mounting on slides, sections are counterstained with eosin, dehydrated and coverslipped.

Western Blot Analysis of Growth Factor Expression

Treated and untreated prostate cell homogenates are examined for expression of growth factors by Western blot analysis. Cell homogenate protein is separated by electrophoresis on SDS-PAGE (7%), then transferred electrophoretically overnight to nitrocellulose paper (Towbin, H., et al., [1979] Proc. Nat. Acad. Sci. 76(9): 4350-4379). The nitrocellulose paper is soaked for one hour at room temperature in 0.5% non-fat dry milk dissolved in phosphate buffered saline, and further soaked overnight at 4° C. in blocking solution (2% bovine serum albumin in 10 mM Tris/0.15 M NaCl/0.1% sodium azide, pH 7.4). The nitrocellulose membranes are incubated with antibodies (IgG fractions of anti-TGF-beta, anti-TGF-alpha, anti-EGF and anti-bFGF) purified by protein A ($1 \times 10^6$ cpm/ml) in blocking buffer for 1 hour. The membrane is washed with PBS containing Nonidet P-40 between incubations. X-O-mat AR2 film (Kodak) is exposed to the membrane at −70° C. and films are developed to examine the expression of growth factors.

Determination of c-fos and c-myc Expression

Expression of c-fos and c-myc in treated and untreated prostatic tissue is determined by Northern blot analysis as follows. Tissue is homogenized in lysis buffer for 15 seconds or until the tissue homogenizes. Sodium acetate is added and the solution is mixed by swirling. An equal volume of water-saturated phenol is added and mixed by inversion, followed by addition of chloroform/isoamyl alcohol. The solution is vortexed vigorously for 30 seconds, and allowed to settle on ice for 15 minutes. The solution is centrifuged for 10-20 minutes at 4° C. After centrifugation, the aqueous phase is carefully aspirated and placed in a new polypropylene tube. One volume of isopropanol is added and the solution is mixed by swirling. The solution is placed in a −20° C. freezer for at least 60 minutes to precipitate RNA. After precipitation, the tube is centrifuged for 10 minutes, and the supernatant is decanted, leaving the RNA pellet. One ml of ethanol is added, and the tube is centrifuged for an additional 10 minutes. The aqueous phase is discarded, and the pellet is washed with 100% ethanol by vortexing. The RNA pellet is redissolved in 0.4 ml of lysis buffer. The RNA is reprecipitated by the addition of 100% ethanol and incubation at −20° C. freezer for at least 60 minutes. The solution is centrifuged and the supernatant discarded. RNA concentration is determined by diluting 5 μL of sample into 995 μL of DEPC water and measuring the ratio of absorbance at 260/280 nm.

The following examples are provided by way of describing specific embodiments without intending to limit the scope of the invention in any way.

EXAMPLE 1

Denervation of the Prostate

Unilateral denervation of the prostate is carried out by removal of the pelvic ganglia, which overlie the prostate of the rat. This approach preserves the functional integrity of the bladder and posterior urethra and removes the possibility for artifact arising from major disturbances in blood flow or micturation. Control animals undergo sham operations without concurrent denervation of the prostate. After denervation, the animals are allowed to recover and maintained prior to collection of the prostate. The prostate is preserved, prepared for light microscopy and examined histologically. The major findings are (1) reduced epithelial cell height primarily due to a decrease in the clear supranuclear zone (due to a reduction in the amount and size of the apical cisternae and the endoplasmic reticulum); (2) major changes in protein expression on SDS gel electrophoresis (the endoplasmic reticulum is important in protein synthesis) (3) modest reduction in the number of secretory granules; (4) an increase in intracellular vacuoles, intercellular empty spaces and reduction in microvilli on the cell surface; and (5) a significant increase in nerve growth factor (NGF) content ipsilateral to the denervation relative to the control group (188±10 vs. 46±20 vs. 29±16 pg/g wet tissue (±SD) NGF is known to influence only sympathetic and sensory neurons. N=15 in both the control and experimental groups.

EXAMPLE 2

Effect of Neurotoxin Injection on Normal Prostate:
Rat Prostate

Rats were randomly assigned into three groups. The first group received a single acute dose of Botulinum toxin type A (BOTOX®, Allergan) of 5, 10 or 15 IU. These animals were sacrificed one week after injection. The second group received a series of 4 weekly injections of 5 IU of Botulinum toxin and were sacrificed at 5 weeks. Control rats received saline injections. Injections were performed as a single or serial injections into the left and/or right ventral lobe of the prostate. note that an injection of methylene blue into one lobe of the rat prostate showed immediate diffusion into the opposite lobe. Thus, there was communication between the prostate lobes and therefore the contralateral lobe could not be used as a true comparative control.

The weight of each prostate ventral lobe collected from healthy animals was approximately 0.50 gram. All toxin-treated animals showed shrinkage of prostate volume, first in the injected lobe, and with subsequent injections, reduction in the overall volume. After four serial injections, the left prostate lobe weighed 0.12-0.17 gram, while the right lobe weighed 0.10-0.14 grams. This represented a reduction of over two-thirds of the original size.

EXAMPLE 3

Effect of Neurotoxin Injection on Urological Dysfunctions:
Human Data

Three patients with recalcitrant voiding dysfunction were treated with injections of botulinum toxin (Botox) as follows. Patient 1 was a 47-year-old male who was incontinent secondary to an injury sustained at the cervical vertebrae (level C6-C7) sustained 14 months previously. Urodynamics on presentation revealed a bladder capacity of 30 cc and a weak sphincter (peak urethral pressure of 40 cm water). He had failed multiple pharmacological regimes and was intolerant to penile clamp/condom devices.

He received four weekly 200 IU botulinum toxin injections into the bladder neck for total dose of 800 IU. Post-injection, his bladder capacities ranged from 300-400 cc with oxybutinin and 150-200 cc without oxybutinin. Peak bladder pressures pre-injection had been 200-cm water, compared to post injection bladder pressures of 40 cm of water. The patient was continent with a penile clamp after treatment with botulinum toxin. In addition, walking and erections improved due to reduced bladder spasticity.

Patient 2 was at 55 year old T12 paraparetic female secondary to traumatic injury 14 years previous. The patient presented with urge incontinence, and had been on self-catheterization every 2 hours during the day and two times at night. The patient received injections into the lateral bladder wall in two weekly injections of 200 IU each for a total of 400 IU of botulinum toxin. The patient's voiding diary data revealed pre-injection capacities of between 150-200 cc. Post injection, diary data indicated bladder capacity increased to 300-400 cc. In addition, the patient no longer had annoying constant urge type dysfunction, slept through the night and was continent on self-catheterization every 4 hours.

Patient 3 was a 65 year old male with disabling perineal pain following radiation treatment for prostatic cancer. The patient had failed medical therapy. He was treated with one 200 IU injection of botulinum toxin into the external urethral sphincter. The patient experienced a dramatic relief of testicle pain and had far less severe pain in the shaft of the penis. Erections were not affected.

EXAMPLE 4

Determination of Smallest Effective Dose

Rats are injected in the prostate ventral lobes with single and serial doses of botulinum toxin (BOTOX®, Allergan). The prostates are harvested at different time intervals to determine the smallest effective dose, as well as the morphological and physiological changes taking place with time. The smallest effective dose is defined as that dose that would demonstrate a decrease in prostate volume.

To assess the response to electrical field stimulation, preparations are mounted between two platinum electrodes placed in the organ bath. The tension of the preparations is adjusted. Transmural stimulation of nerves is performed using a Danted Neuromatic 2000 Stimulator delivering single square-wave pulses at supramaximal voltage with a duration of 0.8 milliseconds at a frequency of 0.5 to 80 hertz. The polarity of the electrodes is changed after each pulse by means of a polarity-changing unit. The train duration is five seconds and the train interval 120 seconds. Isometric tension is recorded by using a Gould thermo-array 8-channel recorder. Separate experiments are performed to determine the preload tension producing optimal responses. In addition, the effect of the electric field stimulation in the presence of different concentrations of individual neuropeptides is determined. These neuropeptides are 10-20 μM adrenaline, 10 μM clonidine, 5-50 mM regitine, 10 mM-0.1 μM acetylcholine, 1-3 μM atropine, 1 nM-10 μM nifedipine, 1-10 nM VIP and 1-250 nM NPY. The effect of nitroprusside (a nitric oxide releasing substance) and methylene blue (a guanylate cyclase inhibitor) on prostate tone and contraction resulting from field stimulation also is examined in these tissues.

EXAMPLE 5

Effect of Botulinum Toxin on Rat Prostatic Tissue: Comparison of Hormonally Intact Rats to Hormonally Deprived Rats To determine if there is any interaction between the neurotoxin and testicularly-derived hormones, studies are performed which will examine the interaction of the neurotoxin with hormonal components. These studies will compare prostatic tissue treated with botulinum toxin harvested from rats that have undergone orchiectomy (hormonally depleted rats) and prostatic tissue from rats treated with botulinum toxin that did not undergo orchiectomy. Fifty-two age-matched rats are treated as described below. Four healthy rats will undergo a sham operation consisting of anesthesia induction, exposure of the prostate and injection of 0.2 cc saline into the left ventral lobe of the prostate. Three rats are given bilateral orchiectomy with no injection to the prostate (hormonally depleted controls), five rats will have orchiectomy and injection of 0.2 ml saline in the left ventral lobe (hormonal depletion+surgical stress control). Four groups of rats receive botulinum injections of 0.5 IU, 1.0 IU, 1.5 IU and 2.5 IU only (hormonally intact experimental rats). Sixteen rats undergo bilateral orchiectomy. Eight of these rats are treated with a single injection of 2.5 IU botulinum toxin into the left ventral lobe 5 weeks after surgery. All rats are sacrificed after six weeks, and the harvested prostate is prepared for examination as described above. A similar atrophic effect on glandular epithelium is expected.

EXAMPLE 6

Effects of Botulinum Toxin on Patients

Patients affected by benign prostatic hyperplasia, abacterial prostatis, or prostatodynia are studied both before and after treatment with botulinum toxin. Patients are eligible for inclusion in this study if they are affected by BPH between the ages of 40 and 80, or if they are between 25 and 60 and have been diagnosed with abacterial prostatitis or prostatodynia. Preferred patients are those who are not good surgical candidates. Patients are evaluated prior to treatment by determination of prostate specific antigen levels (PSA), evaluation of urodynamic parameters (cystometrogram, urethral pressure profile and flowmetry), determination of American Urological Association (AUA) symptom score (Barry, M. J., et al., [1992] J. Urol., 148: 1549-1557), maintenance of a voiding diary, and examination of the prostate by transrectal ultrasound with biopsy (for BPH patients only). One week after initial evaluation is completed, the patient is injected urethroscopically with 200 IU of botulinum toxin as either single unilateral injections, serial unilateral injections or bilateral injections. BPH patients are treated by TURP or undergo control TURP-biopsy 7 days after single injection or 5 weeks after serial injections. The harvested prostatic tissues are prepared for examination as described in Examples 1, 2, 3, and 7-10. The patients are re-evaluated after injection using the same parameters examined during the initial evaluation.

The foregoing description of the invention is exemplary for purposes of illustration and explanation. It will be apparent to those skilled in the art that changes and modifications are possible without departing from the spirit and scope of the invention. All documents cited herein are hereby incorporated by reference. It is intended that the following claims be interpreted to embrace all such changes and modifications.

What is claimed is:

1. A method for treating an urge type dysfunction in a patient, comprising administering a therapeutically effective amount of between 1.4 IU/kg to 17.1 IU/kg of botulinum toxin to a lateral bladder wall of the bladder of the patient, whereby the urge type dysfunction is treated.

2. The method of claim 1, wherein the botulinum toxin is selected from the group consisting of botulinum toxin types A, B, C, D, E, F and G.

3. The method of claim 2, wherein the botulinum toxin is botulinum toxin type A.

4. The method of claim 3, wherein administration is to a bladder wall and administration is by single or serial injection.

5. The method of claim 3, wherein the therapeutically effective amount of botulinum toxin type A is 200 IU of botulinum toxin type A.

6. The method of claim 3, wherein the therapeutically effective amount of botulinum toxin type A is 400 IU of botulinum toxin type A.

7. The method of claim 3, wherein the therapeutically effective amount of botulinum toxin type A is 400 IU of botulinum toxin type A administered serially.

8. The method of claim 1, wherein administration is by injection.

9. The method of claim 8, wherein injection comprises a single injection.

10. The method of claim 8, wherein injection comprises serial injection.

11. The method of claim 1, wherein treating the urge type dysfunction provides the patient with sleep through the night that is uninterrupted by an urge to urinate.

12. The method of claim 1, wherein the botulinum toxin is administered in a pharmaceutically acceptable formulation.

13. A method for treating an urge type dysfunction in a patient, the method comprising administering, via injection, a therapeutically effective amount of between about 1.4 IU/kg and about 17.1 IU/kg of a botulinum toxin type A to a bladder of the patient, whereby the urge type dysfunction is treated.

14. The method of claim 13, wherein the therapeutically effective amount of botulinum toxin type A is 200 IU of botulinum toxin type A.

15. The method of claim 13, wherein the therapeutically effective amount of botulinum toxin type A is 400 IU of botulinum toxin type A.

16. The method of claim 13, wherein the therapeutically effective amount of botulinum toxin type A is 400 IU of botulinum toxin type A administered serially.

17. The method of claim 13, wherein the therapeutically effective amount is provided as a single dose.

18. The method of claim 13, wherein the therapeutically effective amount is provided as a divided dose.

19. The method of claim 13, wherein frequency of urination during sleep is reduced.

20. The method of claim 13, wherein the therapeutically effective amount is administered to a lateral wall of the bladder.

21. The method of claim 13, wherein the botulinum toxin is administered in a pharmaceutically acceptable formulation.

* * * * *